United States Patent [19]

Oppong et al.

[11] Patent Number: 5,198,440
[45] Date of Patent: Mar. 30, 1993

[54] SYNERGISTIC COMBINATIONS OF 2-(THIOCYANOMETHYLTHIO)-BENZOTHIAZOLE WITH HEXAHYDRO-1,3,5-TRIS(2-HYDROXYETHYL)-S-TRIAZINE IN CONTROLLING FUNGAL AND BACTERIAL GROWTH IN AQUEOUS FLUIDS

[75] Inventors: David Oppong, Memphis; C. George Hollis, Germantown, both of Tenn.

[73] Assignee: Buckman Laboratories International, Inc., Memphis, Tenn.

[21] Appl. No.: 759,000

[22] Filed: Sep. 5, 1991

[51] Int. Cl.⁵ .................... A01N 43/66; A01N 43/78
[52] U.S. Cl. ..................................... 514/241; 514/367
[58] Field of Search .................... 514/241, 367

[56] References Cited

U.S. PATENT DOCUMENTS

| | | | |
|---|---|---|---|
| 3,520,976 | 7/1970 | Buckman et al. | 514/367 |
| 4,159,254 | 6/1979 | Grier et al. | 514/241 |
| 4,239,559 | 10/1981 | Buckman et al. | 71/76 |
| 4,479,961 | 10/1984 | Martin | 514/367 |
| 4,595,691 | 6/1986 | LaMarre et al. | 514/367 |
| 4,839,373 | 6/1989 | Ito et al. | 514/367 |
| 4,866,081 | 9/1989 | Ito et al. | 514/367 |
| 4,944,892 | 7/1990 | Leathers et al. | 252/92 |

OTHER PUBLICATIONS

S. P. Denyer, Mechanisms of Action of Biocides, International Biodeterioration, vol. 26 (1990) pp. 89–100.

*Primary Examiner*—Allen J. Robinson
*Attorney, Agent, or Firm*—Finnegan, Henderson, Farabow, Garrett & Dunner

[57] ABSTRACT

Disclosed here are synergistic combinations of 2-(Thiocyanomethylthio)benzothiazole and hexahydro-1,3,5-tris(2-hydroxyethyl)-s-triazine for use in controlling the growth of at least one microorganism, such as fungi and bacteria, in aqueous fluids, such as metalworking fluids. Methods of controlling the growth of at least one microorganism are also disclosed.

17 Claims, No Drawings

SYNERGISTIC COMBINATIONS OF 2-(THIOCYANOMETHYLTHIO)-BENZOTHIAZOLE WITH HEXAHYDRO-1,3,5-TRIS(2-HYDROXYETHYL)-S-TRIAZINE IN CONTROLLING FUNGAL AND BACTERIAL GROWTH IN AQUEOUS FLUIDS

The invention is directed to synergistic combinations of 2-(Thiocyanomethylthio)benzothiazole with hexahydro-1,3,5-tris(2-hydroxyethyl)-s-triazine which are effective microbicides. These synergistic combinations permit the control of fungal and/or bacterial growth in aqueous systems, particularly in metalworking fluids, such as soluble-oil, synthetic and semi-synthetic metalworking fluids.

BACKGROUND OF THE INVENTION 2-(Thiocyanomethylthio)benzothiazole, TCMTB, is known to be useful in controlling bacteria and fungi in various aqueous systems. The preparation and use of 2-(Thiocyanomethylthio)-benzothiazole as a microbicide and a preservative is described in U.S. Pat. No. 3,520,976. U.S. Pat. Nos. 4,293,559, 4,866,081, 4,595,691, 4,944,892, 4,839,373, and 4,479,961 give examples of microbicidal properties of 2-(Thiocyanomethylthio)-benzothiazole. The disclosures of these patents are incorporated herein by reference.

2-(Thiocyanomethylthio)benzothiazole is known to be compatible with soluble oil, semi-synthetic and synthetic metalworking fluids. 2-(Thiocyanomethylthio)-benzothiazole is manufactured by Buckman Laboratories International, Inc., and sold as Busan® 30WB, Busan® 1030, and Busan® 1118. These products are generally aqueous formulations of TCMTB. For example, Busan® 30WB product is a 30% by weight emulsifiable concentrate in water.

Although a good microbicide, 2-(Thiocyanomethylthio)-benzothiazole tends to be ineffective against bacteria under certain conditions, particularly at high pH. Some systems require high concentrations of TCMTB to effectively control the growth of microorganisms. These high concentrations are generally uneconomical.

Hexahydro-1,3,5-tris(2-hydroxyethyl)-s-triazine has been used as a microbicide in the metalworking fluid industry for a long period of time. Hexahydro-1,3,5-tris(2-hydroxyethyl)-s-triazine can be easily prepared starting from formaldehyde and ethanolamine. This compound is known in the trade as "triazine." Triazine is available from many companies as a solid or in varying concentrations in water under such commercial names as Grotan®, Busan® 1060, etc. Triazine is available from Buckman Laboratories, Inc., as Busan® 1060.

As can be seen in Examples 1, 2 and 3, Table 1 (Samples 17-20), Table 2 (Samples 11-14), Table 3 (Samples 9-12), high concentrations of hexahydro-1,3,5-tris(2-hydroxyethyl)-s-triazine are required to control both bacterial and fungal growth in metalworking fluids. One of the undesirable by-products of hexahydro-1,3,5-tris(2-hydroxyethyl)-s-triazine, when used as a microbicide, is formaldehyde. Because of the carcinogenic properties of formaldehyde, it is desirable to use compounds that produce formaldehyde in the smallest quantities possible. However, when used in concentrations which produce only small amounts of formaldehyde, triazine is ineffective against fungi.

Both TCMTB and triazine have been used alone to control microorganisms in industrial fluids. Many industries, such as the machining industry, experience problems in industrial fluids caused by microorganisms. Aqueous metalworking fluids or cutting fluids used in the machining industry are particularly susceptible to fouling caused by microorganisms. In machining operations, metalworking fluids are used primarily to reduce friction and heat, thereby reducing wear and prolonging the life of equipment.

Metalworking fluids have properties which make the fluids ideal for the growth of bacteria and fungi. Although bacteria are important in the biodeterioration of metalworking fluids, fungi and yeast play a similar and important role as well. (Bennett, E. O., "The Deterioration of Metalworking Fluids," Proc. Industrial Microbiology, 13:121 (1974)).

Disadvantageously, these microorganisms can cause buildup of slime/microbial deposits on machine surfaces, the clogging of jets and lines, the deterioration of the properties of the metalworking fluid, enhanced corrosion, health and odor problems. The deterioration of metalworking fluids caused by the growth of microorganisms results in the loss of many of the fluid's essential properties. The pH of the fluid may drop and other chemical changes may occur until the fluid can no longer provide adequate lubrication. At this point, the fluid must be replaced with fresh fluid, which is costly and results in loss of production time.

The problems associated with the growth of microorganisms have resulted in the extensive use of microbicides in metalworking fluid systems. Microbicides may be incorporated in fluid concentrates or added directly to diluted fluids once they are in the holding tanks of the machine works. Of the commercially available microbicides, many have odor problems or create hazards with respect to storage, use or handling. Thus, the commercially available microbicides often possess limited utility. Consequently, workers in the trade have continued to seek improved microbicides.

Economic factors, particularly the cost of the microbicide and the expense of its application, are important when choosing a particular microbicide for use in metalworking fluid systems. The cost performance index of any microbicide is derived from the basic cost of the material, its effectiveness per unit weight, the duration of its biocidal or biostatic effect in the system treated, and the ease and frequency of its addition to the system treated.

Workers in the trade have sought commercially available microbicides capable of exhibiting a prolonged biocidal effect at economical use levels. Physical conditions, such as temperature and chemical reactivity with ingredients present in the system, often diminish or eliminate the effectiveness of known biocides. For example, many systems contain organic material which may react with a biocide and render it ineffective.

SUMMARY OF THE INVENTION

It is an object of this invention to provide a microbicidal composition capable of controlling the growth of at least one microorganism, particularly fungi and bacteria, in aqueous systems over prolonged periods of time. It is an additional object to provide such compositions which are economical to use. A further object of this invention is to provide a microbicidal composition which does not produce large amounts of undesirable by-products such as formaldehyde. Methods of controlling the growth of at least one microorganism in aqueous fluid systems are also objects of this invention.

The above objects can be accomplished by a microbicidal composition comprising (a) hexahydro-1,3,5-tris(2-hydroxyethyl)-s-triazine and (b) 2-(Thiocyanomethylthio)benzothiazole, wherein (a) and (b) are present in an amount synergistically effective to control the growth of at least one microorganism. This composition can be directly added to an aqueous system, such as a metalworking fluid, or added to a concentrate of the metalworking fluid which is subsequently diluted prior to its use.

The present invention also embodies the separate addition of (a) hexahydro-1,3,5-tris(2-hydroxyethyl)-s-triazine and (b) 2-(Thiocyanomethylthio)benzothiazole to aqueous systems, such as metalworking fluids. According to this embodiment, (a) and (b) are individually added to the system so that the final amount of (a) and (b) present in the system at the time of use is that amount synergistically effective to control the growth of at least one microorganism.

DETAILED DESCRIPTION OF THE INVENTION

Metalworking fluid systems in which heavy microbial growth occurs can benefit from the practice of the present invention. The practice of the present invention can also benefit many other aqueous systems, whether or not heavy microbial growth occurs, because it provides a more limited use of hexahydro-1,3,5-tris(2-hydroxyethyl)-s-triazine, a formaldehyde-producing biocide.

In the following discussion of preferred embodiments, component (a) is a hexahydro-1,3,5-tris(2-hydroxyethyl)-s-triazine supplied as Busan ® 1060, a 78.5% by weight solution in water. Component (b) is Busan ® 30WB product which contains 30% by weight of the active ingredient, 2-(Thiocyanomethylthio)benzothiazole or a purified form of the active ingredient, TCMTB, dissolved in an appropriate solvent such as acetone.

As explained above, the amounts of (a) and (b) selected are synergistically effective. In particular, the ratio of component (a) to component (b) preferably ranges from 1:99 to 99:1, more preferably from 20:80 to 80:20, and most preferably is 80:20. A ratio from 40:60 to 60:40 can also be used.

When two chemical microbicides are combined into one product or added separately three results are possible:

1) The resulting product would produce an additive (neutral) effect.
2) The chemicals in the product would produce an antagonistic effect, or
3) The chemicals in the product would produce a synergistic effect.

An additive effect has no economic advantage over the individual components. The antagonistic effect would produce a negative impact. Only synergism, which is less likely to occur than either an additive or antagonistic effect, would produce a positive effect and therefore would be of economic advantage.

It is well-known in the microbicidal literature that there is no theoretical method to provide a reasonable likelihood of knowing, before actually testing, whether an additive, antagonistic or synergistic effect will be obtained when two biocides are mixed to yield a new formulation.

The benefits of the present invention, a synergistic combination of hexahydro-1,3,5-tris(2-hydroxyethyl)-s-triazine and 2-(Thiocyanomethylthio)benzothiazole, can be most evident in fluid systems that are highly contaminated with microorganisms. Highly contaminated systems are those with bacterial and fungal counts greater than $1.0 \times 10^6$/mL which are incapable of experiencing substantial count reduction when treated separately with low concentrations of either 2-(Thiocyanomethylthio)-benzothiazole or Hexahydro-1,3,5-tris(2-hydroxyethyl)-s-triazine.

In these systems, low concentrations of a hexahydro-1,3,5-tris(2-hydroxyethyl)-s-triazine biocide or of a 2-(Thiocyanomethylthio)benzothiazole biocide both fail to provide adequate preservation. Evidence of adequate preservation or control is reduction to and/or maintenance of a bacterial count of less than $1 \times 20^5$ per mL and fungal count of less than $1 \times 10^3$ per mL for a period of not less than about six weeks.

One of the unique features of this invention is that when triazine is used in conjunction with TCMTB, it is possible in many instances, at certain concentrations and ratios of components, to achieve excellent fluid preservation. According to the present invention, control of microbial growth means that the microbial growth, in a highly contaminated system, is reduced to desired levels for fluid preservation, and/or microbial growth is maintained at or below desired levels for fluid preservation.

The synergistic combination of triazine and TCMTB can, not only reduce the total fungal or bacterial count to undetectable limits, but can also maintain that level for a significant period of time. When either of the biocides is used alone at the same concentration of the biocide as used in the synergistic combination each fails to achieve and maintain such a low level of microbial growth.

The synergistic activity of the combinations described above has been confirmed using standard laboratory techniques as illustrated below. The following examples are intended to illustrate, not limit, the present invention.

EXAMPLES

The test method employed was the Standard Method for the Evaluation of Antimicrobial Agents in Aqueous Metalworking Fluids (ASTM Designation: E686-80).

The ASTM test is a multiple challenge test designed to simulate industrial conditions. A formulation of the biocides is added separately to 600 mL aliquots of a metalworking fluid dilution. Controls contained only one of the biocides or no biocide.

The metalworking fluid samples are then inoculated with 1 ml of a mixed, partially defined microbial culture to give an initial bacterial count of approximately $1 \times 10^6$ per mL and an initial fungal count of not less than $1 \times 10^3$ per mL. The system is aerated continuously to provide oxygen for the growth of the microorganisms and also to simulate the industrial rolling of the coolant.

Every week, for a minimum of 6 weeks or until the test fails, the metalworking fluid samples are measured for microbial growth. This is done by enumerating the bacteria and fungi using standard plate-counting techniques.

The microorganisms used in the metalworking fluid inoculum included:

1) *Fusarium sp.* and bacteria obtained from a spoiled industrial fluid.
2) *Staphylococcus aureus*
3) *Pseudomonas aeruginosa*
4) *Klebsiella pneumoniae*
5) *Escherichia coli*

After six weeks a bacterial count of less than $1 \times 10^5$ per mL and fungal count of less than $1 \times 10^3$ per mL indicated adequate preservation. A bacterial or fungal count above these levels indicated a failure to preserve the test fluid.

In general, an effective fungicidal and bactericidal response can be obtained when the synergistic combination is employed in concentrations ranging from about 0.1 to about 5000 ppm of hexahydro-1,3,5-tris(2-hydroxyethyl)-s-triazine, preferably 0.1 to 1000 ppm, and from about 0.1 to about 5000 ppm of 2-(Thiocyanomethylthio)benzothiazole, preferably 0.1 to 500 ppm.

EXAMPLE 1

Synergistic combinations of hexahydro-1,3,5-tris(2-hydroxyethyl)-s-triazine and 2-(Thiocyanomethylthio)benzothiazole for use in soluble oil metalworking fluids.

Component (a) is a 78.5% solution of hexahydro-1,3,5-tris(2-hydroxyethyl)-s-triazine, Busan® 1060 and component (b) is a 30% solution of 2-(Thiocyanomethylthio)benzothiazole, Busan® 30WB. Components (a) and (b) are added in different weight ratios and amounts to the diluted metalworking fluids and tested according to the test methods described previously.

The results are given in Table 1. As can be seen in Table 1, Samples 3 through 13 are all synergistically effective in the control of bacterial and fungal growth. Sample 3 particularly shows the effectiveness of the combination of 250 ppm of component (a) and 100 ppm of component (b) in producing preservative effects. In contrast, when used separately, 2000 ppm of component (a), (Sample 20), are effective and over 1000 ppm of component (b), (Sample 16), are required to preserve the soluble oil metalworking fluid for six weeks.

TABLE 1

Preservation properties of (a) hexahydro-1,3,5-tris(2-hydroxyethyl)-s-triazine and (b) 2-(Thiocyanomethylthio)benzothiazole in soluble oil metalworking fluid.

| Sample | Busan 1060 (a) | Busan 30WB (b) | | Microbial Counts at Indicated Exposure Times (weeks) | | | | | |
|---|---|---|---|---|---|---|---|---|---|
| | | | | 1 | 2 | 3 | 4 | 5 | 6 |
| 1 | 0 | 0 | B | $2.5 \times 10^7$ | $2.4 \times 10^7$ | $1.9 \times 10^7$ | $2.3 \times 10^7$ | $2.8 \times 10^7$ | $3.9 \times 10^7$ |
| 1 | | | F | $3 \times 10^2$ | $10^3$ | $10^3$ | $1.2 \times 10^3$ | $10^3$ | $10^3$ |
| 2 | 250 | 50 | B | 20 | $1.0 \times 10^2$ | 20 | $3.9 \times 10^2$ | $4 \times 10^5$ | $2.3 \times 10^8$ |
| 2 | | | F | <10 | <10 | <10 | <10 | <10 | <10 |
| 3 | 250 | 100 | B | <10 | 50 | 70 | $1.3 \times 10^2$ | <10 | $5.1 \times 10^2$ |
| 3 | | | F | <10 | <10 | <10 | <10 | <10 | <10 |
| 4 | 250 | 250 | B | <10 | 40 | 20 | $3.1 \times 10^2$ | <10 | <10 |
| 4 | | | F | <10 | <10 | <10 | <10 | <10 | <10 |
| 5 | 250 | 500 | B | <10 | 40 | 60 | 50 | <10 | <10 |
| 5 | | | F | <10 | <10 | <10 | <10 | <10 | <10 |
| 6 | 500 | 50 | B | 20 | <10 | <10 | 60 | <10 | <10 |
| 6 | | | F | <10 | <10 | <10 | <10 | <10 | <10 |
| 7 | 500 | 100 | B | 30 | <10 | <10 | $2.0 \times 10^2$ | <10 | $8.2 \times 10^2$ |
| 7 | | | F | <10 | <10 | <10 | <10 | <10 | <10 |
| 8 | 500 | 250 | B | 60 | <10 | <10 | $4.0 \times 10^2$ | <10 | <10 |
| 8 | | | F | <10 | <10 | <10 | <10 | <10 | <10 |
| 9 | 500 | 500 | B | 30 | <10 | <10 | $2.4 \times 10^2$ | 20 | <10 |
| 9 | | | F | <10 | <10 | <10 | <10 | <10 | <10 |
| 10 | 1000 | 50 | B | <10 | <10 | 20 | $2.6 \times 10^2$ | <10 | <10 |
| 10 | | | F | <10 | <10 | <10 | <10 | <10 | <10 |
| 11 | 1000 | 100 | B | 40 | <10 | 30 | $3.8 \times 10^2$ | <10 | <10 |
| 11 | | | F | <10 | <10 | <10 | <10 | <10 | <10 |
| 12 | 1000 | 250 | B | 20 | <10 | <10 | $1.8 \times 10^2$ | <10 | $8.4 \times 10^2$ |
| 12 | | | F | <10 | <10 | <10 | <10 | <10 | <10 |
| 13 | 1000 | 500 | B | 40 | <10 | 20 | $2.7 \times 10^2$ | <10 | <10 |
| 13 | | | F | <10 | <10 | <10 | <10 | <10 | <10 |
| 14 | — | 250 | B | $5.1 \times 10^6$ | $3.0 \times 10^7$ | $3.6 \times 10^7$ | $4.4 \times 10^7$ | $1.4 \times 10^7$ | $2.3 \times 10^7$ |
| 14 | | | F | <10 | <10 | <10 | <10 | <10 | <10 |
| 15 | — | 500 | B | $10^6$ | $8.4 \times 10^6$ | $9.6 \times 10^6$ | $4.1 \times 10^6$ | $1.6 \times 10^7$ | $4.4 \times 10^6$ |
| 15 | | | F | <10 | <10 | <10 | <10 | <10 | <10 |
| 16 | — | 1000 | B | $9.8 \times 10^5$ | $1.8 \times 10^6$ | $1.0 \times 10^7$ | $1.2 \times 10^7$ | $8.4 \times 10^6$ | $4.7 \times 10^6$ |
| 16 | | | F | <10 | <10 | <10 | <10 | <10 | <10 |
| 17 | 250 | — | B | <10 | $2.1 \times 10^7$ | $2.5 \times 10^7$ | $4.5 \times 10^7$ | $3.9 \times 10^7$ | $2.6 \times 10^7$ |
| 17 | | | F | $5.1 \times 10^4$ | $3 \times 10^5$ | $3.3 \times 10^5$ | $6.2 \times 10^5$ | $2.7 \times 10^5$ | $2.5 \times 10^5$ |
| 18 | 500 | — | B | $2.0 \times 10^2$ | <10 | $10^6$ | $3.3 \times 10^7$ | $3.0 \times 10^7$ | $3.0 \times 10^7$ |
| 18 | | | F | $9.4 \times 10^2$ | $1.0 \times 10^6$ | $1.9 \times 10^6$ | $7 \times 10^6$ | $1.2 \times 10^6$ | $1.3 \times 10^6$ |
| 19 | 1000 | — | B | 80 | <10 | <10 | $10^3$ | $4.5 \times 10^6$ | $7.1 \times 10^7$ |
| 19 | | | F | <10 | $3.8 \times 10^2$ | $5.9 \times 10^5$ | $1.3 \times 10^6$ | $2.0 \times 10^6$ | $5.0 \times 10^6$ |
| 20 | 2000 | — | B | <10 | <10 | <10 | $1.8 \times 10^3$ | $1.9 \times 10^2$ | <10 |
| 20 | | | F | <10 | 20 | <10 | <10 | <10 | <10 |

B = Bacterial count (cfu/mL)
F = Fungal count (cfu/mL)
1 Entries indicate amount of formulation

EXAMPLE 2

Synergistic combinations for hexahydro-1,3,5-tris(2-hydroxyethyl)-s-triazine and 2-(Thiocyanomethylthio)benzothiazole for use in synthetic metalworking fluids.

Component (a) is a 78.5% solution of hexahydro-1,3,5-tris(2-hydroxyethyl-s-triazine, Busan® 1060 product, and component (b) is a purified solid 2-(Thiocyanomethylthio)benzothiazole. Components (a) and (b) are added in different weight ratios and amounts to the diluted metalworking fluids and tested according to the test methods described previously.

The results are given in Table 2. As can be seen in Table 2, samples 5,6,7,9 and 10 show a synergistic result in the effective control of bacterial and fungal growth in the metalworking fluid.

When used alone, 2000 ppm of component (a), (Sample 14), are effective and over 300 ppm of component (b), (Sample 17), are required to preserve the synthetic metalworking fluids for six weeks. In contrast, when used in combination, only 500 ppm of component (a) and only 75 ppm of component (b) are needed to produce the same effect (Sample 5)

EXAMPLE 3

Synergistic combinations of hexahydro-1,3,5-tris(2-hydroxyethyl)-s-triazine and 2-(Thiocyanomethylthio)benzothiazole for use in semi-synthetic metalworking fluids.

Component (a) is a 78.5% solution of hexahydro-1,3,5-tris(2-hydroxyethyl)-s-triazine, Busan® 1060, and component (b) is a 30% solution of 2-(Thiocyanomethylthio)benzothiazole, Busan® 30WB. Components (a) and (b) are added in different weight ratios and amounts to the diluted metalworking fluids and tested according to the test methods described previously.

The results are given in Table 3. As can be seen in Table 3, sample 3 through 8 show a synergistic result in the effective control of bacterial and fungal growth in the metalworking fluid. When used separately, either 2000 ppm of component (a), (Sample 12), are effective or over 1000 ppm of component (b) (Sample 15) are required to produce the desired preservative effect. But a combination of 250 ppm of component (a) and 300 ppm of component (b) (Sample 3) can produce the same preservative effect.

TABLE 2

Preservation properties of (a) hexahydro-1,3,5-tris(2-hydroxyethyl)-s-triazine and (b) 2-(Thiocyanomethylthio)benzothiazole in a synthetic metalworking fluid.

| Sample | Busan 1060 (a) | TCMTB (b) | | 1 | 2 | 3 | 4 | 5 | 6 |
|---|---|---|---|---|---|---|---|---|---|
| 1 | 0 | 0 | B | $1.4 \times 10^8$ | $3.6 \times 10^8$ | $5.3 \times 10^7$ | $10^8$ | $2.1 \times 10^8$ | $4 \times 10^8$ |
| 1 | | | F | $1.8 \times 10^5$ | $8 \times 10^5$ | $10^5$ | $10^6$ | $3 \times 10^5$ | $2.1 \times 10^6$ |
| 2 | 250 | 75 | B | $5.7 \times 10^3$ | $2.1 \times 10^3$ | 50 | $1.5 \times 10^4$ | $2.5 \times 10^7$ | $8.6 \times 10^7$ |
| 2 | | | F | <10 | <10 | $1.1 \times 10^3$ | $1.1 \times 10^6$ | $1.3 \times 10^6$ | $3.2 \times 10^6$ |
| 3 | 250 | 150 | B | $4.8 \times 10^3$ | $1.6 \times 10^3$ | $2.8 \times 10^3$ | $2.5 \times 10^3$ | $2.0 \times 10^2$ | $2.0 \times 10^5$ |
| 3 | | | F | <10 | <10 | <10 | <10 | $4.1 \times 10^3$ | $2.4 \times 10^6$ |
| 4 | 250 | 300 | B | $3.5 \times 10^3$ | $5.0 \times 10^3$ | $1.4 \times 10^3$ | $8.2 \times 10^2$ | 80 | $7.0 \times 10^2$ |
| 4 | | | F | <10 | <10 | <10 | <10 | 40 | $9.8 \times 10^5$ |
| 5 | 500 | 75 | B | $4.5 \times 10^3$ | <10 | $3.8 \times 10^2$ | <10 | 40 | $2.0 \times 10^2$ |
| 5 | | | F | <10 | <10 | <10 | <10 | <10 | <10 |
| 6 | 500 | 150 | B | $4.2 \times 10^3$ | $2.1 \times 10^2$ | $8.0 \times 10^2$ | <10 | <10 | <10 |
| 6 | | | F | <10 | <10 | <10 | <10 | <10 | <10 |
| 7 | 500 | 300 | B | 80 | <10 | <10 | <10 | <10 | <10 |
| 7 | | | F | <10 | <10 | <10 | <10 | <10 | <10 |
| 8 | 1000 | 75 | B | 60 | 60 | <10 | <10 | <10 | $3.0 \times 10^7$ |
| 8 | | | F | <10 | <10 | <10 | <10 | $4.5 \times 10^3$ | $8.2 \times 10^5$ |
| 9 | 1000 | 150 | B | 50 | <10 | <10 | <10 | 80 | <10 |
| 9 | | | F | <10 | <10 | <10 | <10 | <10 | <10 |
| 10 | 1000 | 300 | B | 20 | <10 | <10 | 20 | 30 | <10 |
| 10 | | | F | <10 | <10 | <10 | <10 | <10 | <10 |
| 11 | 250 | — | B | <10 | $5.6 \times 10^6$ | $2.1 \times 10^8$ | $2 \times 10^9$ | $10^9$ | $2.2 \times 10^8$ |
| 11 | | | F | $5 \times 10^4$ | $4.8 \times 10^5$ | $5.2 \times 10^5$ | $10^6$ | $5 \times 10^5$ | $10^6$ |
| 12 | 500 | — | B | <10 | $4.6 \times 10^2$ | $1.9 \times 10^7$ | $1.7 \times 10^7$ | $5.2 \times 10^7$ | $5.9 \times 10^7$ |
| 12 | | | F | $4.4 \times 10^3$ | $7.8 \times 10^6$ | $1.4 \times 10^6$ | $10^6$ | $1.0 \times 10^6$ | $6 \times 10^5$ |
| 13 | 1000 | — | B | <10 | <10 | $3.9 \times 10^3$ | $10^7$ | $10^8$ | $3.3 \times 10^8$ |
| 13 | | | F | <10 | $1.2 \times 10^2$ | $3.5 \times 10^5$ | $9 \times 10^5$ | $4.1 \times 10^6$ | $10^6$ |
| 14 | 2000 | — | B | <10 | <10 | <10 | <10 | <10 | <10 |
| 14 | | | F | <10 | <10 | <10 | <10 | <10 | 40 |
| 15 | — | 75 | B | $8.7 \times 10^3$ | $7.5 \times 10^3$ | $1.4 \times 10^7$ | $5.9 \times 10^7$ | $3.1 \times 10^7$ | $5.6 \times 10^7$ |
| 15 | | | F | <10 | <10 | <10 | <10 | <10 | <10 |
| 16 | — | 150 | B | $2.5 \times 10^3$ | $1.6 \times 10^6$ | $2.8 \times 10^7$ | $5.7 \times 10^7$ | $6.4 \times 10^7$ | $4.6 \times 10^7$ |
| 16 | | | F | <10 | <10 | <10 | <10 | <10 | 30 |
| 17 | — | 300 | B | $7.7 \times 10^3$ | $1.4 \times 10^3$ | $10^6$ | $7.1 \times 10^7$ | $2.6 \times 10^7$ | $5.9 \times 10^7$ |
| 17 | | | F | <10 | <10 | <10 | <10 | <10 | <10 |

B = Bacterial count (cfu/mL)
F = Fungal count (cfu/mL)
2 Entries indicate amount of formulation for component (a) and amount of pure product for component (b).

TABLE 3

Preservation properties of (a) hexahydro-1,3,5-tris(2-hydroxyethyl)-s-triazine and (b) 2-(Thiocyanomethylthio)benzothiazole in a semi-synthetic metalworking fluid.

| Sample | Busan 1060 (a) | Busan 30W (b) | | 1 | 2 | 3 | 4 | 5 | 6 |
|---|---|---|---|---|---|---|---|---|---|
| 1 | 0 | 0 | B | $1.6 \times 10^7$ | $3.7 \times 10^8$ | $10^9$ | $1.1 \times 10^8$ | $4.2 \times 10^8$ | $3.7 \times 10^7$ |
| 1 | | | F | $1.0 \times 10^5$ | $10^5$ | $10^5$ | $3 \times 10^5$ | $2 \times 10^6$ | $3 \times 10^5$ |
| 2 | 250 | 50 | B | <10 | 20 | <10 | $6.9 \times 10^3$ | $1.5 \times 10^5$ | $1.2 \times 10^5$ |
| 2 | | | F | <10 | <10 | <10 | <10 | <10 | <10 |
| 3 | 250 | 100 | B | <10 | 40 | <10 | $2.6 \times 10^3$ | $3.8 \times 10^2$ | $4 \times 10^3$ |
| 3 | | | F | <10 | <10 | <10 | <10 | <10 | <10 |
| 4 | 250 | 250 | B | <10 | 20 | <10. | $2.1 \times 10^3$ | $8.2 \times 10^2$ | $5.3 \times 10^3$ |
| 4 | | | F | <10 | <10 | <10 | <10 | <10 | <10 |
| 5 | 500 | 50 | B | <10 | <10 | <10 | $3.9 \times 10^3$ | $1.1 \times 10^2$ | $4.9 \times 10^3$ |
| 5 | | | F | <10 | <10 | <10 | <10 | <10 | <10 |
| 6 | 500 | 100 | B | <10 | <10 | <10 | $3.1 \times 10^3$ | $1.7 \times 10^2$ | $5.1 \times 10^3$ |
| 6 | | | F | <10 | <10 | <10 | <10 | <10 | <10 |
| 7 | 500 | 250 | B | <10 | <10 | <10 | $6.1 \times 10^2$ | $1.9 \times 10^2$ | $7 \times 10^3$ |
| 7 | | | F | <10 | <10 | <10 | <10 | <10 | <10 |
| 8 | 1000 | 50 | B | <10 | <10 | <10 | $3.6 \times 10^2$ | 70 | $1.7 \times 10^3$ |
| 8 | | | F | <10 | <10 | <10 | <10 | <10 | <10 |
| 9 | 250 | — | B | <10 | $2.9 \times 10^6$ | $3.5 \times 10^7$ | $2.0 \times 10^7$ | $3.2 \times 10^7$ | $2.5 \times 10^7$ |
| 9 | | | F | $5.8 \times 10^5$ | $9.8 \times 10^6$ | $2.2 \times 10^6$ | $10^6$ | $2.2 \times 10^6$ | $1.7 \times 10^6$ |
| 10 | 500 | — | B | <10 | $2.1 \times 10^2$ | $7.3 \times 10^6$ | $1.4 \times 10^7$ | $2.5 \times 10^7$ | $2.9 \times 10^7$ |
| 10 | | | F | <10 | $9.7 \times 10^5$ | $9.7 \times 10^5$ | $10^6$ | $2 \times 10^6$ | $2.8 \times 10^6$ |
| 11 | 1000 | — | B | <10 | <10 | $2.6 \times 10^4$ | $10^5$ | $5.9 \times 10^6$ | $1.9 \times 10^7$ |
| 11 | | | F | <10 | <10 | $2.4 \times 10^5$ | $1.2 \times 10^6$ | $1.9 \times 10^6$ | $2.6 \times 10^6$ |
| 12 | 2000 | — | B | <10 | <10 | <10 | <10 | <10 | <10 |
| 12 | | | F | <10 | <10 | <10 | <10 | <10 | <10 |
| 13 | — | 250 | B | <10 | $6 \times 10^6$ | $2.3 \times 10^7$ | $1.0 \times 10^8$ | $9.6 \times 10^7$ | $7.9 \times 10^7$ |
| 13 | | | F | <10 | <10 | <10 | <10 | <10 | <10 |
| 14 | — | 500 | B | <10 | $1.4 \times 10^6$ | $10^7$ | $9.9 \times 10^7$ | $1.0 \times 10^8$ | $8.3 \times 10^7$ |
| 14 | | | F | <10 | <10 | <10 | <10 | <10 | <10 |
| 15 | — | 1000 | B | <10 | $10^5$ | $1.3 \times 10^7$ | $1.6 \times 10^7$ | $1.0 \times 10^7$ | $4.3 \times 10^6$ |
| 15 | | | F | <10 | <10 | <10 | <10 | <10 | <10 |

Column headers: Biocide Levels (ppm) — Busan 1060 (a), Busan 30W (b); Microbial Counts at Indicated Exposure Times (weeks) — 1, 2, 3, 4, 5, 6.

B = Bacterial count (cfu/mL)
F = Fungal count (cfu/mL)
3 Entries indicate amount of formulation.

As seen from the above examples, compositions comprising triazine and TCMTB ca possess synergistic antifungal and antibacterial activity. The compositions can be employed at appropriate concentrations to control, and even inhibit, the growth of fungi and bacteria in aqueous systems such as metalworking fluids.

The required synergistically effective amounts (concentrations) will vary depending on the particular organisms and particular applications, and can readily be determined by routine experimentation. Use of a synergistically effective amount of triazine (a) and TCMTB (b) enables the use of a substantially smaller amount of each component to achieve the desired effect than would be necessary for each component if used alone, or than would be necessary if a mere additive effect from combining (a) and (b) were obtained.

What is claimed is:

1. A microbicidal composition comprising (a) hexahydro-1,3,5-tris(2-hydroxyethyl)-s-triazine and (b) 2-(Thiocyanomethylthio)benzothiazole, wherein (a) and (b) are present in an amount synergistically effective to control the growth of at least one bacterium.

2. The composition of claim 1, wherein the ratio of (a) and (b) is from 1:99 to 99:1.

3. The composition of claim 2, wherein said ratio is from 20:80 to 80:20.

4. The composition of claim 1, wherein the concentration of (a) ranges from 0.1 ppm to 5000 ppm and the concentration of (b) ranges from 0.1 ppm to 5000 ppm.

5. A metalworking fluid comprising: a fluid and
   (a) hexahydro-1,3,5-tris(2-hydroxyethyl)-s-triazine and
   (b) 2-(Thiocyanomethylthio)benzothiazole; wherein (a) and (b) are present in an amount synergistically effective to control the growth of at least one bacterium.

6. The metalworking fluid of claim 5, wherein the ratio of (a) to (b) is from 1:99 to 99:1.

7. A method of controlling the growth of at least one bacterium in an aqueous fluid comprising the step of separately adding to a diluted aqueous fluid
   (a) hexahydro-1,3,5-tris(2-hydroxyethyl)-s-triazine and
   (b) 2-(Thiocyanomethylthio)benzothiazole;
wherein the combined amount of separately added (a) and (b) is synergistically effective to control the growth of said bacterium in said fluid.

8. The method of claim 7, wherein said aqueous system is a metalworking fluid.

9. The method of claim 7, wherein the ratio of (a) to (b) after addition of both (a) and (b) to said fluid is from about 99 to 99:1.

10. A method of controlling the growth of at least one bacterium in an aqueous fluid comprising the step of adding to an aqueous fluid an effective amount of the composition according to claim 1.

11. The method of claim 10, wherein said aqueous fluid is a metalworking fluid.

12. The method of claim 11, wherein said aqueous fluid is a soluble oil metalworking fluid.

13. The method of claim 11, wherein said aqueous fluid is a semi-synthetic metalworking fluid.

14. The method of claim 11, wherein said aqueous fluid is a synthetic metalworking fluid.

15. The method of claim 11, wherein the ratio of (a) and (b) is from 1:99 to 99:1.

16. The method of claim 14, wherein said ratio is from 20:80 to 80:20.

17. The method of claim 16, wherein said ratio is from 40:60 to 60:40.

* * * * *

UNITED STATES PATENT AND TRADEMARK OFFICE
CERTIFICATE OF CORRECTION

PATENT NO. : 5,198,440
DATED : March 30, 1993
INVENTOR(S) : David OPPONG and C. George HOLLIS It is certified that error appears in the above-identified patent and that said Letters Patent is hereby corrected as shown below:

Claim 9, column 10, line 50, delete "about 99" and insert
--about 1:99--.

Signed and Sealed this

Twenty-first Day of December, 1993

Attest:

BRUCE LEHMAN

*Attesting Officer*    *Commissioner of Patents and Trademarks*